(12) United States Patent
Geisler et al.

(10) Patent No.: US 7,888,128 B2
(45) Date of Patent: Feb. 15, 2011

(54) METHOD FOR DETERMINING SURFACTANT CONCENTRATION IN AQUEOUS SOLUTIONS

(75) Inventors: Richard Geisler, Glen Allen, VA (US); John Richardson, Ashland, VA (US)

(73) Assignee: Chem Treat, Inc., Glen Allen, VA (US)

( * ) Notice: Subject to any disclaimer, the term of this patent is extended or adjusted under 35 U.S.C. 154(b) by 1678 days.

(21) Appl. No.: 10/639,480

(22) Filed: Aug. 13, 2003

(65) Prior Publication Data

US 2005/0037509 A1 Feb. 17, 2005

(51) Int. Cl.
*G01N 33/00* (2006.01)
(52) U.S. Cl. .................. 436/164; 436/163; 422/55; 422/61; 422/68.1; 422/82.09
(58) Field of Classification Search .................. 422/55, 422/61, 68.1, 82.09; 436/163, 164
See application file for complete search history.

(56) References Cited

U.S. PATENT DOCUMENTS

| 3,725,006 A | 4/1973 | Brandstrom et al. |
| 3,969,076 A | 7/1976 | Wang |
| 3,992,149 A | 11/1976 | Wang |
| 5,710,048 A | 1/1998 | Ernst et al. |

OTHER PUBLICATIONS

Hiroshi Nakamura et al., *Determination of Critical Micelle Concentration of Anionic Surfactants by Capillary Electrophoresis Using 2-Naphthalenemethanol as a Marker for Micelle Formation*, Analytical Sciences, Apr. 1998, vol. 14, The Japan Society for Analytical Chemistry, Shinjuku, Tokyo, Japan.

Xirong Huang et al., *Determination of the Critical Micelle Concentrations of Cationic Surfactants*, Journal of Chemical Education, Jan. 1999, vol. 76, No. 1, Jinan, China.

Norika Nagamine et al., *Measurement of Critical Micelle Concentrations of Cationic Surfactants by Capillary Electrophoresis*, Analytical Sciences, Apr. 1998, vol. 14, The Japan Society for Analyitcal Chemistry, Shinjuku, Tokyo, Japan.

*Primary Examiner*—Lyle A Alexander (57) ABSTRACT

The present method provides a single-phase technique in which an ionic strength adjuster and a water insoluble dye are added to a sample of an aqueous solution containing an unknown quantity of a known surfactant. Even at surfactant concentrations well below the critical micelle concentration (CMC) of the aqueous sample, the addition of an ionic strength adjuster induces the surfactant to form micelles. These micelles absorb the water insoluble dye, thereby imparting a known color to the aqueous sample being tested. The color intensity of the treated aqueous sample is directly related to the concentration of the surfactant in the sample and, through the use of calibration curves prepared from samples of know concentration, can be used to determine the surfactant concentration.

20 Claims, 5 Drawing Sheets

METHOD FOR DETERMINING SURFACTANT CONCENTRATION IN AQUEOUS SOLUTIONS

FIELD OF THE INVENTION

This invention relates to analytical methods for quantifying the surfactant concentration in an aqueous working fluid. In particular, this invention relates to analytical methods for measuring the concentration of surfactant additives in aqueous systems such as boiler and chiller systems. More particularly, this invention pertains to a colorimetric method for quantitatively measuring the surfactant content of an aqueous working fluid.

BACKGROUND OF THE INVENTION

Aqueous based working fluids encompass a broad spectrum of liquids, for example, machining fluids, hydraulic fluids, coolants and heat transfer fluids. The aqueous heat transfer fluids are widely used in boiler and chiller systems and are typically treated with one or more additives to improve the performance of the fluid and/or protect the wetted components of the system including pipes, valves, pumps and heat transfer surfaces. Organic lubricants may be used to reduce friction and heat production and reduce or prevent wear of contacting parts. Corrosion inhibitors may be used to reduce or prevent metallic, or in some cases non-metallic, corrosion or other degradation of the system components.

Biocides and fungicides may be used reduce or prevent microbial or fungal growth within the system. Other additives may be used to prevent or reduce foaming, precipitation of metal contaminants, scale formation or misting. Aqueous systems also frequently include one or more surfactants (i.e., surface active agents) that may contribute to the system lubrication and/or maintaining a stable suspension of water insoluble particles within the working fluid.

The properties of aqueous working fluid compositions, particularly those in boiler systems operating under high cycles of concentration (also referred to as COC or Cycles) are known to change both qualitatively and quantitatively over a period of use. This is particularly true for systems with severe operating conditions (e.g., high temperatures, high solids, and high shear forces). These changes may be the result of one or more factors such as evaporation, reactions (e.g., oxidation or corrosion), thermal degradation and physical degradation of one or more components of the aqueous working fluid composition or the system equipment.

Controlling, preventing and/or compensating for the anticipated chemical and/or physical changes in aqueous working fluids and/or the additive package during use is important to the economic and functional utility of these fluids. As an example, an additive package and a monitoring scheme that will control corrosion of a boiler condensate system, maintain the heat transfer performance, and/or extend the periods between maintenance shutdowns will have a direct beneficial economic impact on the overall system performance. In this regard, it is important to measure and monitor the content or effectiveness of various constituents of the aqueous based functional fluid during use and/or storage. Likewise, measurement of constituent concentration during manufacture is required to exercise quality control of the fluid produced.

The present invention relates generally to measurement of the surfactant concentration in aqueous working fluids. Anionic surfactants are prevalent in, and are often the preferred surfactant in aqueous working fluid composition and concentrated chemical additive packages for the treatment of aqueous systems. Given the wide use of surfactants in aqueous systems, a number of analytical techniques have been developed for determining the surfactant concentration of an aqueous working fluid.

Many of these prior art techniques have utilized two-phase titration techniques for measuring the anionic surfactant content. Two-phase titration techniques typically involve the titration of the anionic surfactant present in a known quantity of the aqueous working fluid (e.g., boiler water or chiller water) with a cationic titrant in the presence of a two-phase water/organic solvent (e.g., chloroform) system in the presence of an indicator. During the titration, a colored complex is formed in the aqueous phase and extracted into the organic solvent layer, signaling the endpoint of the titration. This same basic procedure is then repeated using a known quantity of one or more standards comprising an aqueous solution of the anionic surfactant having a known concentration. The amount of the aqueous cationic surfactant solution titrant necessary to reach the endpoint during the titration of the sample and standard solutions may then be used to calculate the amount of anionic surfactant present in the sample.

While performing such a two-phase titration procedure, it is necessary to shake or otherwise agitate the samples being titrated frequently in order to insure complete reaction between the surfactant and titrant and to promote the movement of the colored complex formed during the titration from the aqueous phase and into the organic solvent layer. It is also necessary to select an organic solvent that is essentially water insoluble and an appropriate indicator capable of forming a colored complex with the cationic titrant that is both essentially water insoluble and soluble in the organic solvent. It is especially preferred that the generally water-insoluble colored complex also have a color that may be easily distinguished from the color or colors assumed by the indicator when in water.

This two-phase titration procedure, while capable of producing generally accurate and repeatable concentration data, has several disadvantages. In particular, the two-phase technique is time consuming, requires frequent shaking of the samples, is dependent on the effectiveness of the shaking to obtain complete reaction, requires an organic solvent with the incumbent disposal problems and health concerns and may be relatively expensive.

In order to address at least some of these deficiencies, efforts have been made to develop an acceptable single-phase test technique. One such technique is disclosed in Ernst et al.'s U.S. Pat. No. 5,710,048, entitled "Determination of Surfactant Concentration in an Aqueous Fluid." The single-phase technique disclosed by Ernst et al. comprises the steps of adjusting the pH of the test sample including an anionic surfactant to within a selected range of pH values, adding an indicator (toluidine blue) to the sample, adding a known amount of a standardized aqueous solution of 1,3-didecyl-2-methylimidazolium halide to the sample and indicator, and then titrating with a standardized aqueous solution of a polyvinylsulfuric acid alkali metal salt until a blue to pink color change is obtained. Once the amount of titrant needed is determined, the quantity of anionic surfactant in the original sample may be determined from one of a series of pH range specific standard curves. In this manner, Ernst et al. can provide a quantitative measurement of the anionic surfactant concentration without the need for a separated organic solvent phase and the inherent difficulties associated with using such a solvent. There remains a need, however, for simple, repeatable single-phase tests for determining the surfactant concentration in an aqueous system.

BRIEF SUMMARY OF THE INVENTION

The present method provides a single-phase technique in which an ionic strength adjuster and a water insoluble dye are added to a sample of an aqueous solution containing an unknown quantity of a known surfactant. At surfactant concentrations well below the critical micelle concentration (CMC) of a low ionic strength aqueous solution, an ionic strength adjuster is used to induce the surfactant to form micelles. These micelles absorb the water insoluble dye, thereby imparting a known color to the aqueous sample being tested. The color intensity of the treated aqueous sample is directly related to the concentration of the surfactant in the sample and, through the use of calibration curves prepared from samples of know concentration, can be used to determine the surfactant concentration.

DETAILED DESCRIPTION OF THE INVENTION

Surfactants are substances that drastically lower surface tension, a term derived from their function as surface active agents. Surfactants tend to be strongly absorbed at air-water interfaces, include both polar and non-polar portions and may generally be categorized as cationic, anionic or nonionic. Examples of anionic surfactants include sodium stearate, sodium oleate, sodium dodecyl sulfate and dodecyl benzene sulfonate. Examples of cationic surfactants include dodecylamine hydrochloride and hexadecyltrimethyl ammonium bromide. Examples of nonionic surfactants include polyethylene oxides, sorbitan esters (spans) and polyoxyethylene sorbitan esters (tweens).

At low concentrations surfactants can form an aqueous solution with some of the surfactant molecules absorbing onto vessel walls or at the air/water interface. As the surfactant concentration increases, additional surfactant molecules are attracted to the air/water interface surface and eventually form a monolayer.

Figure 1:
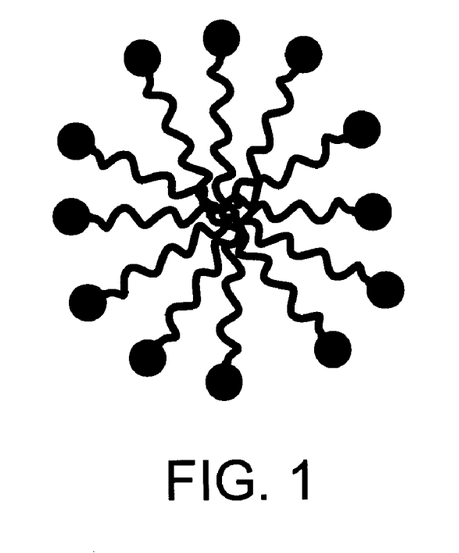
FIG. 1 illustrates a simple micelle structure.
Figure 2:
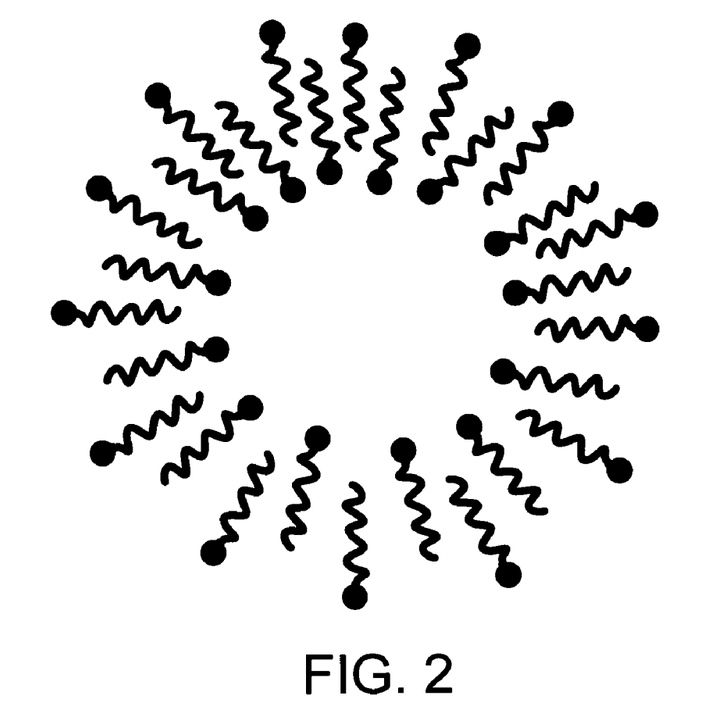
FIG. 2 illustrates a more complex micelle structure in which the surfactant molecules assume a membrane-like structure.

With increasing surfactant concentration, or with certain changes in other solution parameters, collections of oriented surfactant molecules can form micelles in which the surfactant molecules form a generally spherical shape with the hydrophobic portions toward the center with the hydrophilic portions forming the outer surface of the sphere, as represented in FIG. 1, or may form a more complex structure in which the surfactant molecules form a membrane-like structure with hydrophilic portions arranged as both an inner and an outer layer with the hydrophobic portions being more centrally located. The surfactant concentration at which micelles begin to form (the process of micellization) is referred to as the critical micelle concentration (CMC). There is a relatively small range of surfactant concentrations separating the limit below which virtually no micelles are detected and the limit above which substantially all additional surfactant molecules will form micelles. The CMC for a particular surfactant/solvent system can be measured by plotting one or more properties of the surfactant solution against the surfactant concentration. The relationship between the property and the concentration is usually noticeably different above and below the CMC, allowing extrapolation of the two data sets to approximate the CMC. The CMC depends in part on the molecular structure of the surfactant. For example, for anionic surfactants, increasing the length of the hydrophobic portion of the surfactant molecule increases the tendency to form micelles.

Indeed, adding several carbons to the hydrophobic portion can lower the CMC by an order of magnitude or more. With ionic micelles, the addition of simple electrolytes tends to reduce the repulsion between charged groups at the surface of the micelle, thereby decreasing the CMC. Similarly, the addition of other organic molecules to the surfactant solution can affect the CMC. For instance, molecules that promote the formation of sugars will tend to lower the CMC while molecules that disrupt urea and formamide structures will tend to increase the CMC. Further, once a surfactant solution has reached its CMC, it can solubilize organic materials that are generally insoluble in water by incorporating them into the organic interior of the micelles.

The apparent solubility of surfactants that can be induced to form micelles will increase rapidly once the solution has reached a certain minimum temperature that is referred to as the Krafft point or Krafft temperature. At the Krafft point, the previously unassociated surfactant molecules, with their somewhat limited solubility, organize into highly soluble micelles that include multiple surfactant molecules. As the temperature of the surfactant solution is increased, the solubility slowly increases until, at the Krafft temperature, the CMC is reached and micelles are formed throughout the solution.

Micelles can be characterized by a micellar molecular weight ($M_r$), which represents the molecular weight of the surfactant molecules comprising an average micelle, and/or an aggregation number (N), which is the number of surfactant molecules incorporated into an average micelle. In general, surfactants with a lower CMC tend to have a higher $M_r$. Both the CMC and the $M_r$ are affected by temperature, pH and ionic strength. The critical micellar temperature (CMT) is the minimum temperature at which the surfactant will form micelles and the cloud point is the temperature above which surfactant micelles will form super aggregates.

As discussed above, it is well known that under a range of conditions aqueous surfactant solutions at or above the CMC can form colloidal particles called micelles. The CMC for a particular surfactant solution can be determined by various techniques including surface tension, conductivity, and spectroscopy. A simple method for the determination of CMC involves the addition of a water insoluble dye to an aqueous surfactant solution and then slowly increasing the surfactant concentration.

At surfactant concentration levels below the CMC the dye remains undissolved and thus will not produce a significant spectroscopic response. However, when the surfactant concentration reaches the CMC, the water insoluble dye can penetrate and dissolve within the micelle, thereby imparting the dye color to the aqueous solution. Although this technique is useful for determining the CMC for a particular surfactant system, it does not provide a means for accurately determining the surfactant concentration at levels significantly above or below the CMC.

The present invention provides a means for measuring surfactant concentrations well below the normal CMC by providing a scaleable response at surfactant concentrations on the order of 1-2 ppm, levels more in keeping with modern water treatment compositions. The present method involves adjusting the ionic strength of an aqueous surfactant to induce the formation of micelles at levels well below the normal CMC and thereby obtain a scaleable response to surfactant concentration that can be quantified spectroscopically after the addition of a suitable water insoluble dye.

The method of the present invention advantageously provides a convenient method for quickly and accurately field-testing the low levels of surfactant typically used in modern water treatment formulations. The availability of this test will allow improved surfactant monitoring, reduced surfactant use and reduced chemical costs. The method of the present invention allows an operator to easily determine the surfactant concentration of an aqueous system at levels orders of magnitude lower than the traditional CMC for that system in the absence of ionic strength adjustment.

The method according to the present invention will be particularly useful in measuring the low concentrations of surfactant-based materials used as corrosion inhibitors in steam generation/condensate equipment to provide a protective film on the metal surfaces. Quick and accurate measurement of these surfactant components will insure that effective surfactant dosage levels can be maintained within the steam generation/condensate system while minimizing the risk of over-feeding, expensive and unnecessary, or under-feeding, which increases the risk of corrosion or scaling.

For example, for a certain surfactant utilized in steam condensate systems, the CMC was determined to be approximately 50 ppm based on cloud point data. However, the typical concentration at which this surfactant was used in the steam condensate system was less than 2 ppm. Consequently, a method for accurately determining the surfactant concentration at levels of less than 5%, and often on the order of 2%, of the normal CMC value was needed to monitor treatment levels of the surfactant. Initial efforts to induce micelle formation with an ionic strength adjuster in the presence of water insoluble dye introduced as a discrete powder or in an organic solvent were generally unsatisfactory. Continued efforts to develop a satisfactory test led to the development of a reagent formulation of the dye that could be utilized to introduce the dye composition into the test solution at particle size able to penetrate the surfactant micelle particles more effectively.

Regardless of the dye composition selected for use according to this invention, it is preferred that the colorimetric measurements be taken at a wavelength at or relatively near the wavelength of peak absorbance. This wavelength for any particular dye composition may be determined by scanning a sample prepared by dissolving the dye composition in an organic solvent and measuring the absorbance over a wide range of wavelengths, typically the range will include at least the visible and near visible IR and UV wavelengths.

Once a preferred wavelength or preferred wavelength range has been identified, it is preferable to perform a series of periodic measurements on a representative sample to determine the reaction time necessary for the absorption of the dye to be essentially complete. For example, absorption measurements can be made each minute after combining the surfactant sample, the ionic strength modifier and the dye reagent method. These periodic measurements will then be continued until the degree of absorbance at the selected wavelength stabilizes.

Depending on the condition of the sample, colloidal or other suspended particles may interfere with the absorbance measurements. These concerns may be addressed in various ways including filtering the sample to remove larger suspended solids without removing the surfactant monomers or simply allowing a sufficient period to allow particles other than the micelles to settle to a level in the sample cell where they will not significantly degrade the measurement. In general, when executing the measurement method according to the present invention, the operator will want to use the minimum reaction/settling time that provides repeatable results.

Similarly, it is preferable to determine the appropriate degree of ionic strength adjustment and quantity of water insoluble dye that will provide a reproducible and scaleable response at and around the surfactant concentration levels of interest in the system being tested. It is contemplated that by following this basic protocol, a series of calibration curves can be developed for each combination of ionic strength adjuster, dye and surfactant or combination or surfactants that is or may be used in a particular aqueous system. Once a combination of ionic strength adjuster ("ISA") and dye has been determined and calibration curves prepared, the resulting test method can be used in field locations as well as laboratory environments.

Figure 3:
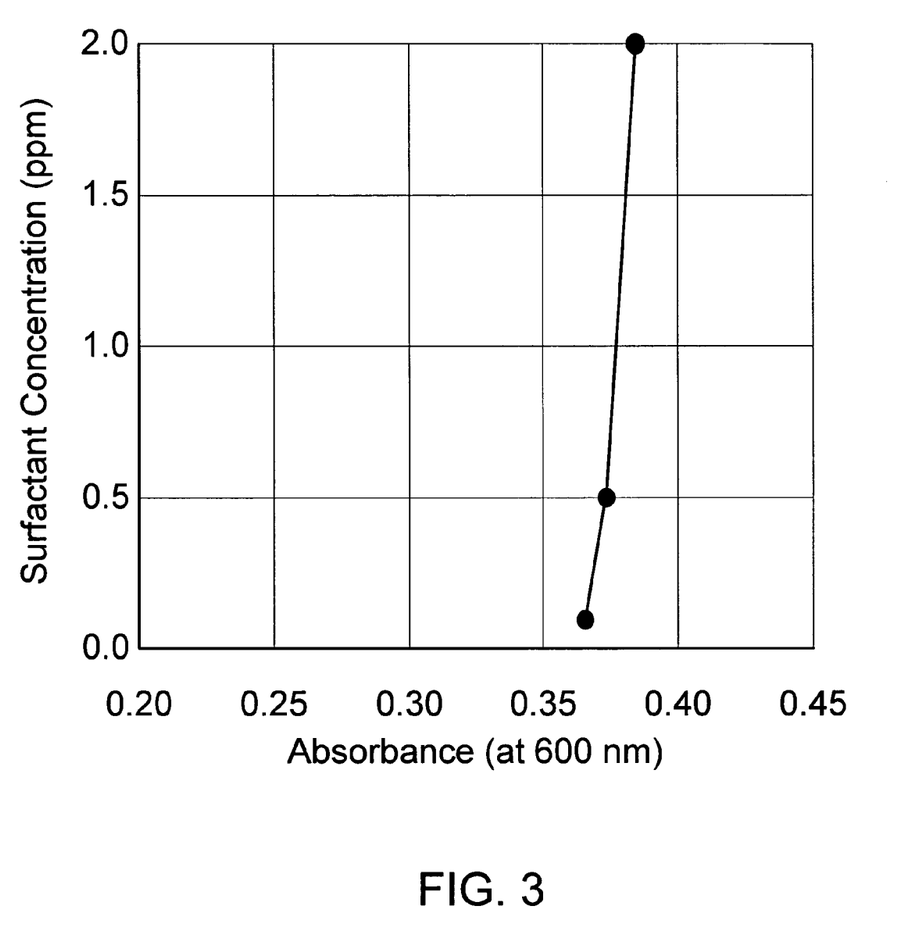
FIG. 3 illustrates the surfactant concentration/absorbance response relationship for a water insoluble dye (Sudan Red 7b at 600 nm) for the surfactant polyethylene glycol monooleate (PEG) at concentrations of up to 2 ppm without ionic strength adjustment.

In accord with the procedures outlined above, FIG. 3 shows the surfactant concentration/absorbance response at 600 nm for an aqueous sample containing polyethylene glycol monooleate with Sudan Red 7b dye in the absence of any ionic strength adjustment. As reflected in the data, without ionic strength the absorbance response does not vary significantly over the surfactant concentration range (0-2 ppm) that may typically be employed in a steam condensate system.

Figure 4:
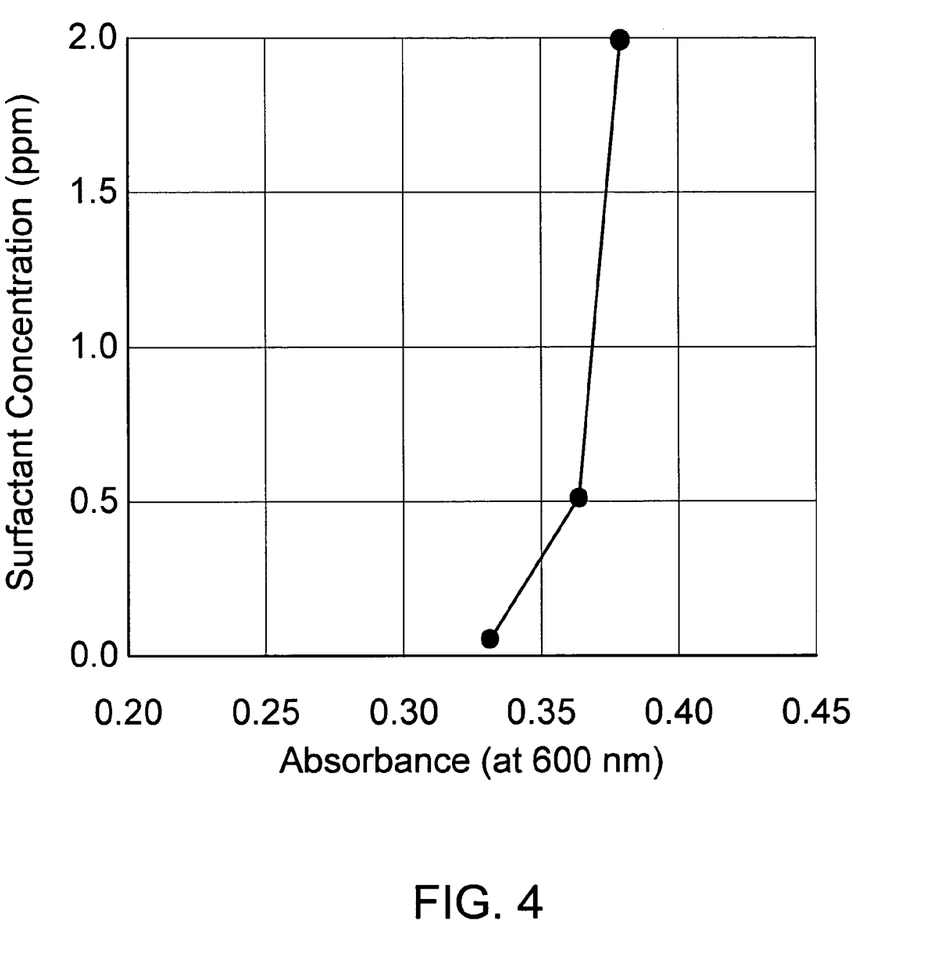
FIG. 4 illustrates the surfactant concentration/absorbance response relationship for a water insoluble dye (Sudan Red 7b at 600 nm) for PEG concentrations of up to 2 ppm with a high level of ionic strength adjustment.

Similarly, FIG. 4 reflects the surfactant concentration/absorbance response at 600 nm for an aqueous sample containing polyethylene glycol monooleate with Sudan Red 7b dye after a high (approximately 200,000 ppm) degree of ionic strength adjustment and a reaction/settling period of about 5 minutes. As reflected in the data, the absorbance response does not vary significantly over the 0-2 ppm concentration range of interest.

Figure 5:
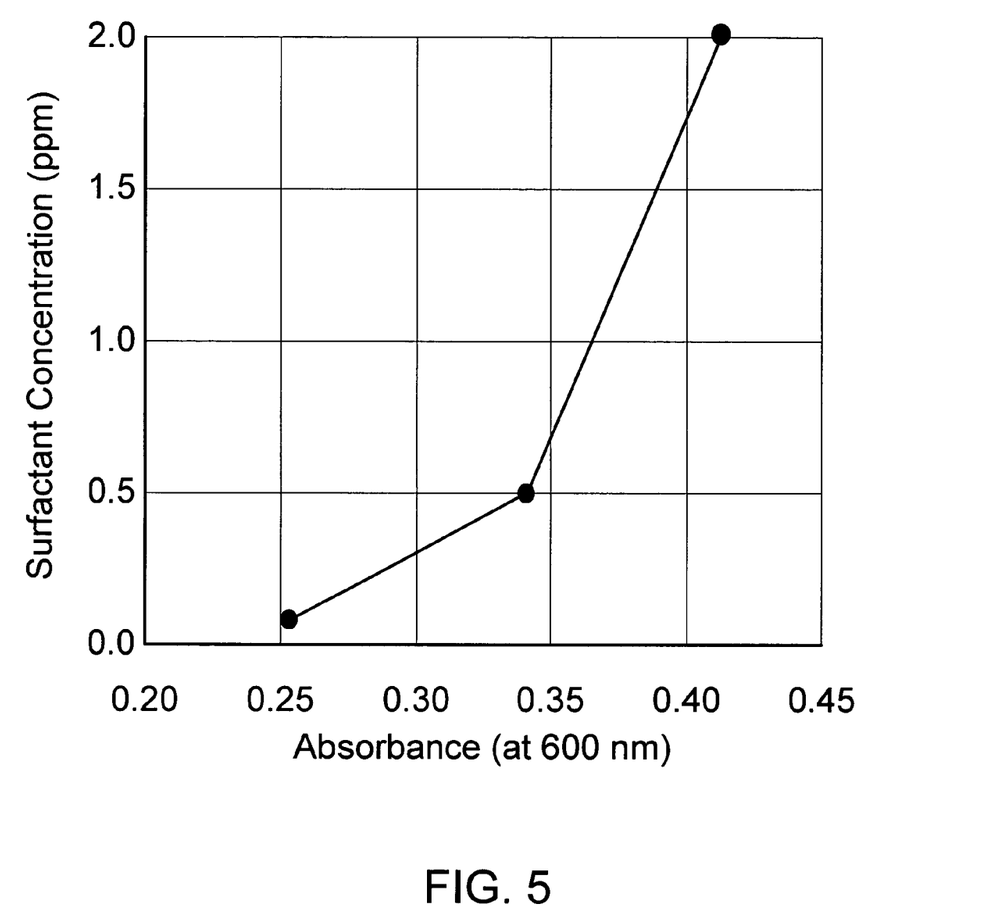
FIG. 5 illustrates the surfactant concentration/absorbance response relationship for a water insoluble dye (Sudan Red 7b at 600 nm) for PEG concentrations of up to 2 ppm with an intermediate level of ionic strength adjustment.

FIG. 5, however, reflects the surfactant concentration/absorbance response at 600 nm for an aqueous sample containing polyethylene glycol monooleate with Sudan Red 7b dye with an intermediate (approximately 100,000 ppm) degree of ionic strength adjustment and a reaction/settling time of about 5 minutes. As reflected in the data, in this instance there was a significant degree of variation in the absorbance response over the concentration range of interest. Indeed, the response provides two substantially linear ranges that together allow for a quantitative calibration of the response.

Figure 6:
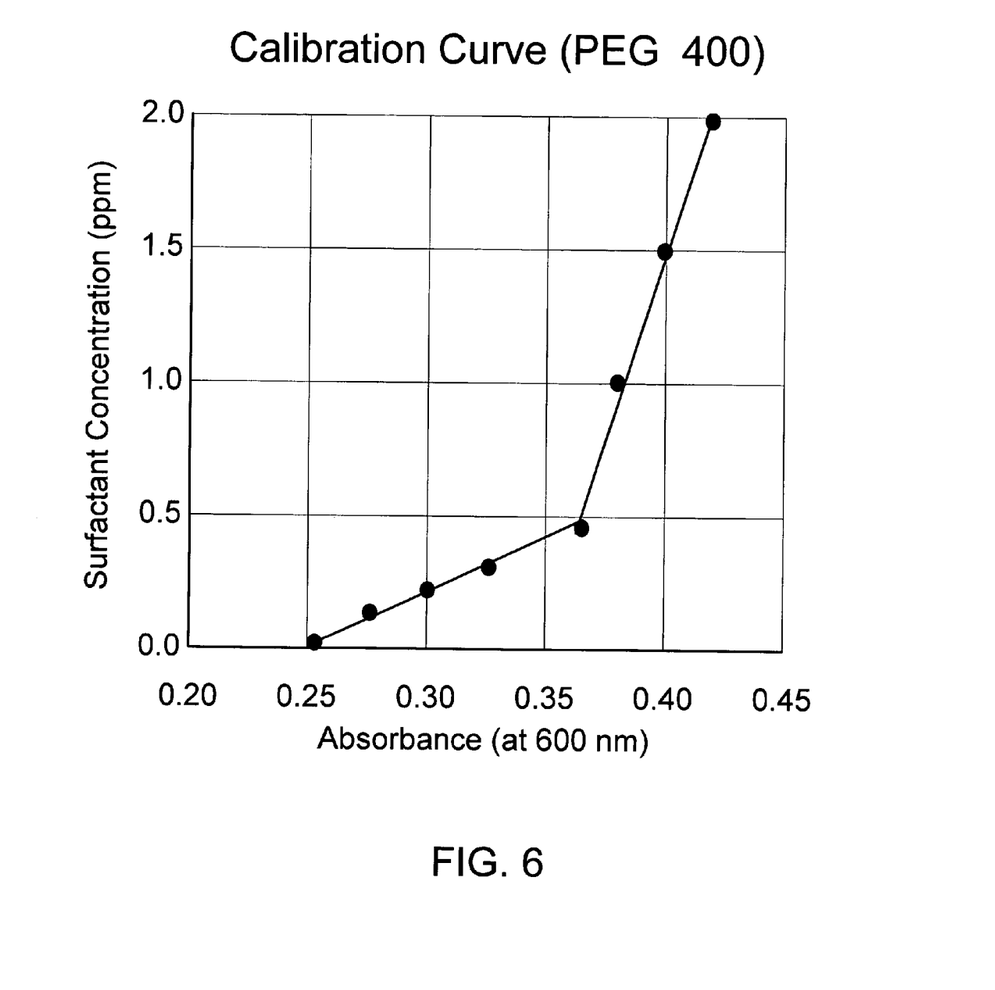
FIG. 6 illustrates a calibration curve prepared for PEG using Sudan Red 7b at 600 nm and an intermediate level of ionic strength adjuster.

FIG. 6 reflects an individual calibration curve prepared for the polyethylene glycol monooleate (PEG) with an intermediate level of ionic adjustment using a Sudan Red 7b dye composition for a surfactant concentration range of 0-2 ppm.

The amount of ISA required depends on the type and concentration of the surfactant. An excess quantity of an ISA will tend to lower the CMC to a level below the desired operating range of the test. Conversely, an insufficient quantity of an ISA will not lower the CMC sufficiently to be within the desired operating range of the test. The determination of the appropriate quantity range for an ISA for use with a target surfactant/solution system is required to ensure repeatable concentration results. The particle size and form of the dye will also affect the operation of the test, with those dyes available with a discrete, reproducible particle size provided in a solid matrix being preferred to reduce, and preferably eliminate, the potential impact of dye solvents on the test results.

The preferred sequence for conducting a surfactant concentration evaluation according to the present invention comprises adding the predetermined quantity of the ISA to the sample, agitating the sample to ensure that the ISA is fully dissolved and the micelles are formed. A predetermined quantity of the selected dye is then added to the solution, after which the sample is subjected to additional agitation for a period of time sufficient to allow the dye to penetrate the micelles and form the sample test solution. The sample test solution is then maintained for a predetermined period of time to allow for substantially complete color development. A portion of the sample test solution is then subjected to a color analysis, typically at a wavelength at or near, or across a wavelength range encompassing the wavelength of maximum adsorption for the specific dye being utilized.

This test procedure may also be implemented in a field test kit that includes one or more reagents or standard solutions, including at least one ionic strength adjuster and a dye, a test cell, and a color comparison chart or, preferably, color comparator tubes arranged around the test cell, that will allow the operator to estimate the surfactant concentration based on the observed color of the test solution when a spectrometer is not readily available. In use, the operator would draw a predetermined volume of treated water from the aqueous system, add predetermined quantities of the provided reagents and typically agitate the test solution and, after a predetermined reaction time, "read" the color of the test solution in the test cell by comparing the resulting color to the provided standards. Depending on the volumes used and the nature of the reagents and treated water, the test solution preparation may be conducted directly in the test cell or may be conducted in a separate vessel or vessels, with a smaller quantity being later transferred to the test cell to be "read." As will be appreciated, such field test kits can be tailored for aqueous systems having various surfactants and properties by selecting different combinations of ionic strength adjusters and dyes to obtain a sufficiently reproducible result for the surfactant concentration range of interest. As will also be appreciated, depending on the state of the aqueous system being tested, filtration and/or a settling time may be necessary to reduce the influence of suspended matter on the repeatability and accuracy of the operator's observation of the color of the test solution. P This test procedure may by adapted to utilize generally any water insoluble dye. In particular, it is believed that any dye selected from a group consisting of Acid Blue 45, Alizarin Saphirol B, Acid Green 25, Alizarian Cyamine Green B, Acridrine Orange, Basic Orange 14, Acridrine Orange Base, Solvent Orange 15, Acridrine Orange HCL, Acriflavine HCL, Acriflavine Neutral, Alizarin, Mordant Red 11, Aliazarin Complexon, Alizarin Red S, Mordant Red 3, Aliazarin Yellow G (G), Aliazarin Yellow G (R), Alizarin Yellow R, Mordant Orange 1, Alizarin Yellow R Sodium Salt, Mordant Yellow 3R, Alkali 6B, Acid Blue 110, Amido Black 10B, Acid Black 1, 1-Amino-2-Naphthol-4-Sulfonic Acid, Aniline Blue W/S, Acid Blue 93:1, Auramine O, Basic Yellow 2, Azure A, Azure B (Azure I), Azure C, Azure II, Azure II Eosinate, Benzopurpurin 4B, Direct Red 2, Biebrich Scarlet, Acid Red 66, Bismark Brown R, Basic Brown 4, Bismark Brown Y, Basic Brown 1, Brilliant Black BN, Naphthol Black, Brilliant Blue G250, Acid Blue 90, Brilliant Blue R250, Acid Blue 83, Brilliant Cresyl Blue, Basic Dye, Brilliant Crocein MOO, Acid Red 73, Brilliant Green, Basic Green 1, Bromo Phenol Red, Carmine (Alum Lake), Natural Red 4, Carminic Acid 50%, Natural Red 4, Carminic Acid 95%, Natural Red 4, Celestine Blue B, Mordant Blue 14, Chicago Sky Blue 6B, Direct Blue, China Blue, Acid Blue 22, Chloro Phenol Red, Chocolate Brown, Food Brown 3, Chrome Azurol S, Mordant Blue 29, Chromotrope 2B, Acid Red 176, Chromotrope 2R, Acid Red 29, Chromoxane Cyanine R, Mordant Blue 3, Chrysophenine, Direct Yellow 12, Congo Red, Direct Red 28, Cresyl Violet Acetate, Cresyl Fast Violet, Crystal Violet, Basic Violet 3, Curcumin, Natural Yellow 3, Dibromofluorescein, Acid Orange II, Direct Blue 71/td, Sirius Light Blue BRR, Eosin B, Acid Red 91, Eosin B Spirit Soluble, Eosin Y Free Acid, Solvent Red 43, Eosin Y Sodium Salt, Acid Red 87, Erichrome Black T, Mordant Black 11, Erichrome Blue Black B, Mordant Black 3, Erichrome Blue Black R, Mordant Black 17, Erichrome Cyanine R, Mordant Blue 3, Erioglaucine, Acid Blue 9, Erythrosine B, Acid Red 51, Erythrosine B Free Acid, Solvent Red 140, Ethyl Eosin, Solvent Red 45, Ethyl Orange, Ethyl Violet, Basic Violet, Evans Blue, Direct Blue 53, Fast Blue B-Salt, Fast Green FCF, Food Green 3, Fast Sulphon Black F, Acid Black 32, Fluorescein, Solvent Yellow 94, Fluorescein Complexon, Fluorescein W/S, Acid Yellow 73, Fuchsin Acid, Acid Violet 19, Fuchsin Basic, Basic Red 9, Fuchsin Basic, Basic Violet 14, Gallocyanine, Mordant Blue 10, Gentian Violet, Basic Violet 3, Giemsa Stain, Guiney Green B, Acid Green 3, Hematein, Hematoxylin, Natural Black 1, Indigo Carmine, Acid Blue 74, Indione Blue, Indocyanine Green, Indophenol Blue, Janus Green B, Jenner Stain, Lacmoid, Leishman Stain, Leuco Crystal Violet, Light Green S.F., Acid Green 5, Lissamine Green B, Malachite Green, Basic Green, Malachite Green Oxalate, Basic Green 4, Martius Yellow, Acid Yellow 24, May-Grundwald Stain, Metanil Yellow, Acid Yellow 36, Methyl Green, Methylene Blue, Basic Blue 9, Methylene Green, Basic Green 5, Methylene Violet 3RAX, Methyl Blue, Acid Blue 93:1, Methyl Green, Basic Blue 20, Methyl Violet 2B, Basic Violet 1, Napthol Green B, Acid Green 1, Neutral Red, Basic Red 5, New Coccine, Acid Red 18, New Methylene Blue N, Basic Blue 24, Nigrosin W/S, Acid Black 2, Nile Blue A Chloride, Nile Blue A Sulphate, Basic Blue, Nile Red, Ninhydrin, Nuclear Fast Red, Calcium Red, Oil Red O, Solvent Red 27, Orange II, Acid Orange 7, Orange IV, Acid Orange 5, Orange G, Acid Orange 10, Orcein, Pararosaniline Acetate, Pararosaniline HCL, Basic Red 9, Patent Blue A, Acid Blue 7, Patent Blue VF, Acid Blue 1, Patent Blue Violet, Acid Blue 3, Phenosafranin, 4-Phenylazophenol, Solvent Yellow 7, Phloxime B, Acid Red 92, Plasmocorinth B, Mordant Blue 13, Ponceau 4R, Acid Red 18, Ponceau S, Acid Red 112, n' Propyl Red, Purpurin, Quinoline Yellow, Solvent Yellow 33, Quinoline Yellow, Acid Yellow 3, Reactive Red 4, Resazurin, Resazurin sodium salt, Rhodamine B, Basic Violet 10, Rhodamine 6G, Basic Red 1, Rose Bengal, Acid Red 9, Rosolic Acid, Aurin, Saffron, Natural Yellow 6, Safranine 0, Basic Red 2, Sirius Red, Direct Red 80, Stains-All, Sudan Black B, Solvent Black 3, Sudan II, Solvent Orange 7, Sudan III, Solvent Red 23, Sudan IV, Solvent Red 24, Sudan Orange G, Solvent Orange 1, Sudan Red 7B, Solvent Red 19, Tatra Bromo Phenol Blue, Tartrazine, Thionin acetate, Titan Yellow, Direct Yellow 9, Toluidine Blue 0, Basic Blue 17, Tropaeolin 0, Acid Orange 6, Trypan Blue, Direct Blue 14, Victoria Blue B, Basic Blue 26, Victoria Blue R, Basic Blue 11, Water Blue 1, Acid Blue 22, Wright's Stain, Xylene Cyanol FF, Acid Blue 147, Xylene Cyanol FF, Xylidine Ponceau 2R, Acid Red 26, Zincon and Monosodium Salt could be used successfully in such a test procedure.

Similarly, it is believed that the concentration of a number of surfactants, including those classed as nonionic surfactants, such as alkyloxypolyethyleneoxyethanol, octylphenoxypolyethoxyethanol, polyoxyethylene surfactants (ethoxylates), carboxylic acid esters, carboxylic amides and polyalkylene oxide block copolymers, cationic surfactants, such as amines, 2-alkyl-1-(2-hydroxyethyl)-2-imidazolines and quarternary ammonia salts, anionic surfactants, such as sodium dodecyl diphenyloxide disulfonate, sodium dodecylbenzene sulfonate, sodium xylene sulfonate, carboxylates, acylated protein hydrolysates, sulfonates, sulfates and phosphate esters, or amphoteric surfactants, such as cocoamidopropyl betaine and imidazolinium derivatives could be evaluated successfully by applying a test procedure according to the present invention. Similarly, the surfactant concentration evaluation according to the present invention may utilize a range of ionic strength adjusters, such as NaOH, NaCl, $NaNO_3$, KCl, $CaCl_2$, $(HN)_2SO_4$, $NH_4OH$ and $NH_4Cl$, that may be used singly or in combination to suppress the CMC of the test solution.

It will be understood that the above described preferred embodiment(s) of the present invention are susceptible to various modifications, changes, and adaptations, and the same are intended to be comprehended within the meaning and range of equivalents of the appended claims. In particular, it is anticipated that other combinations of surfactants, ion strength adjusters and dye compositions, as well as mixtures thereof, would be suitable for use in the present invention.

Further, although a number of equivalent components may have been mentioned herein which could be used in place of the components illustrated and described with reference to the preferred embodiment(s), this is not meant to be an exhaustive treatment of all the possible equivalents, nor to limit the invention defined by the claims to any particular equivalent or combination thereof. A person skilled in the art would realize that there may be other equivalent components presently known, or to be developed, which could be used within the spirit and scope of the invention defined by the claims.

We claim:

1. A method of determining a surfactant concentration below the critical micelle concentration ("CMC") of the surfactant in an aqueous solution comprising the steps of:
    a) collecting a sample of the aqueous solution having a surfactant concentration below the CMC;
    b) adding an ionic strength adjuster to the sample to induce a suppressed CMC for the surfactant;
    c) adding a dye composition to the sample, the dye composition being generally insoluble in water;
    d) maintaining the sample for a predetermined reaction period to prepare a test solution;
    e) measuring the absorbance of the test solution at a wavelength to obtain an absorbance value; and
    f) comparing the absorbance value with a calibration curve to determine the surfactant concentration of the aqueous solution.

2. A method of determining a surfactant concentration in an aqueous solution according to claim 1, further comprising the step of:
    b.1) preparing a reagent comprising a generally water-insoluble dye composition, the reagent being characterized by a known concentration of the dye composition, wherein adding a dye composition to the sample further comprises:
    adding a quantity of the reagent to the sample, wherein the quantity of the reagent is sufficient to achieve a predetermined concentration of the dye composition in the sample.

3. A method of determining a surfactant concentration in an aqueous solution according to claim 1, wherein:
    the surfactant is polyethylene glycol monooleate;
    the dye composition is Sudan Red 7b;
    the ionic strength adjuster is calcium chloride; and
    the surfactant concentration of the sample is less than 5 ppm.

4. A method of determining a surfactant concentration in an aqueous solution according to claim 3, wherein:
    the surfactant concentration of the sample is less than 2 ppm.

5. A method of determining a surfactant concentration in an aqueous solution according to claim 1, further comprising the steps of:
    b1) agitating the sample after adding the ionic strength adjuster for a predetermined mixing period.

6. A method of determining a surfactant concentration in an aqueous solution according to claim 5, wherein:
    the mixing period is between about 10 seconds and 1 minute; and
    the reaction period is between about 1 minute and 10 minutes.

7. A method of determining a surfactant concentration in an aqueous solution according to claim 6, wherein:
    the mixing period is approximately 30 seconds; and
    the reaction period is approximately 5 minutes.

8. A method of determining a surfactant concentration in an aqueous solution according to claim 1, wherein:
    the wavelength is between about 200 nm and about 800 nm.

9. A method of determining a surfactant concentration in an aqueous solution according to claim 3, wherein:
    the wavelength is between about 550 nm and about 650 nm.

10. A method of determining a surfactant concentration in an aqueous solution according to claim 9, wherein:
    the wavelength is approximately 600 nm.

11. A method of determining a surfactant concentration in an aqueous solution according to claim 1, further comprising the step of:
    a1) filtering the sample through a filter medium, the filter medium having a degree of porosity sufficient to remove particulates from the sample while allowing substantially all of the surfactant to pass through the filter medium.

12. A method of determining a surfactant concentration below a critical micelle concentration ("CMC") of the surfactant in an aqueous solution comprising the steps of:
    a) collecting a sample of the aqueous solution having a surfactant concentration below the CMC;
    b) adding an ionic strength adjuster to the sample to induce a suppressed CMC for the surfactant;
    c) adding a dye composition to the sample, the dye composition being generally insoluble in water;
    d) maintaining the sample for a predetermined reaction period to prepare a test solution;
    e) visually comparing the test solution with a plurality of standards corresponding to known micelle concentration levels to approximate the surfactant concentration of the aqueous solution.

13. A method of determining a surfactant concentration in an aqueous solution according to claim 12, wherein:
    the plurality of standards include a graduated series of reference solutions.

14. A method of determining a surfactant concentration in an aqueous solution according to claim 12, wherein:
the plurality of standards include a graduated series of colored regions.

15. A method of determining a surfactant concentration in an aqueous solution according to claim 12, wherein:
the surfactant is polyethylene glycol monooleate;
the dye composition is Sudan Red 7b;
the ionic strength adjuster is calcium chloride; and
the surfactant concentration of the sample is less than 5 ppm.

16. A method of determining a surfactant concentration in an aqueous solution according to claim 12, further comprising the steps of:
b1) agitating the sample after adding the ionic strength adjuster for a predetermined mixing period.

17. A method of determining a surfactant concentration in an aqueous solution according to claim 16, wherein:
the mixing period is between about 10 seconds and 1 minute; and
the reaction period is between about 1 minute and 10 minutes.

18. A field test kit for determining a surfactant concentration in an aqueous solution using the method according to claim 12 and without utilizing electrically powered equipment, comprising:
a) a sample vessel;
b) a container of an ionic strength adjuster solution;
c) a container of a dye composition;
d) a test solution cell arranged in close proximity to a plurality of standards corresponding to known micelle concentration levels reflecting a plurality of aqueous solutions containing less than 5% of a CMC value of the surfactant.

19. The field test kit for determining a surfactant concentration in an aqueous solution using a method according to claim 18, wherein:
the sample vessel and the test solution cell are a single receptacle.

20. A method of determining a surfactant concentration below the critical micelle concentration ("CMC") of the surfactant in an aqueous solution comprising the steps of:
a) collecting a sample of the aqueous solution having a surfactant concentration of less than 5% of the CMC of the surfactant in the aqueous solution;
b) treating the sample with a sufficient quantity of an ionic strength adjuster to the sample to induce a suppressed CMC for the surfactant and adding a dye composition to produce a treated sample, the dye composition being generally insoluble in water;
d) maintaining the treated sample for a predetermined reaction period to prepare a test solution;
e) measuring the absorbance of the test solution at a wavelength to obtain an absorbance value; and
f) comparing the absorbance value with a calibration curve to determine the surfactant concentration of the aqueous solution.

* * * * *